(12) United States Patent
Lichkus et al.

(10) Patent No.: US 6,855,278 B2
(45) Date of Patent: Feb. 15, 2005

(54) PROCESS OF MAKING A DENTAL PROSTHESIS

(75) Inventors: Andrew M. Lichkus, York, PA (US); William James Schiffer, Jr., Dover, PA (US); Craig L. Nalbone, York, PA (US); Michael L. DeCavalcante, Camp Hill, PA (US)

(73) Assignee: Dentsply Research & Development Corp.

( * ) Notice: Subject to any disclaimer, the term of this patent is extended or adjusted under 35 U.S.C. 154(b) by 282 days.

(21) Appl. No.: 10/016,924

(22) Filed: Dec. 14, 2001

(65) Prior Publication Data

US 2002/0068258 A1 Jun. 6, 2002

Related U.S. Application Data

(63) Continuation of application No. 09/362,364, filed on Jul. 28, 1999, now abandoned.

(51) Int. Cl.⁷ ..................... A61C 13/007; A61C 13/01; A61C 13/20; B29C 45/14; B29C 45/16
(52) U.S. Cl. ......................... 264/18; 264/245; 264/255; 264/275; 264/279
(58) Field of Search .................... 264/18, 245, 255, 264/275, 279

(56) References Cited

U.S. PATENT DOCUMENTS

| | | |
|---|---|---|
| 3,628,248 A | 12/1971 | Kroder et al. |
| 4,247,665 A | 1/1981 | Daniels et al. |
| 4,412,824 A | 11/1983 | Kulwiec et al. |
| 4,514,173 A | 4/1985 | Re |
| 4,659,752 A | 4/1987 | Piret |
| 4,956,130 A * | 9/1990 | Sonner ........................ 264/18 |
| 5,102,337 A | 4/1992 | Soroca |
| 5,122,571 A | 6/1992 | Westeppe et al. |
| 5,254,604 A | 10/1993 | Mori et al. |
| 5,288,799 A | 2/1994 | Schmid et al. |
| 5,551,873 A | 9/1996 | Aiba |
| 5,569,036 A | 10/1996 | Goldiner et al. |
| 5,607,300 A | 3/1997 | Tepper |
| 5,623,013 A | 4/1997 | Tanaka et al. |
| 5,658,586 A | 8/1997 | Rajaiah et al. |
| 6,136,920 A | 10/2000 | Hert et al. |

FOREIGN PATENT DOCUMENTS

| | | |
|---|---|---|
| DE | 196 18 364 A1 | 11/1997 |
| WO | 96/13244 A1 | 5/1996 |

OTHER PUBLICATIONS

Fitton et al; Clinical Materials 17 (1994) ; "The Physical Properties of a Polyacetal Denture Resin"; pp. 125–129.
Morton et al; The Journal of Prosthetic Dentistry; vol. 80, No. 1 Evaluation of resilient abutment components on measured strain using dynamic loading conditions; pp. 46–51 (Jul. 1998).

Valplast Internatioanl Corp.; Smile with Confidence, Valplast brochure, 1996; 3 pages.
Valplast International Corp.; For Your Next Flexible Partial, Valplast brochure, 1995; 2 pages.
Valplast International Corp.; "Valplast® Techniques", Valplast brochure, 1995; 5 pages.
Valplast Processing Technique 1995 (34 pages).
Rapid Injection Systems; Clasp–eze brochure; 1 page (undated).
Rapid Injection Systems (RIS) Machine (3 pages) (undated).
Flexite II; Specifically for Partials (3 pages) (undated).
Flexite and Northern technique Manual; 35 pages (undated).
Rapid Injection Systems Corp.; Instructions for Claspeze; 1 page (undated).
Pressing Dental S.r.l.; Technical table 005; Partial Denture Manufacturing Procedure (2 pages) (undated).
Acetal Dental; Acetalyc Resin Injection Process; The.r.mo. Free; Polymethylmethacrylate ohne Monomer Das thermoplastische Polymer fur Totalprothesen; 6 pages (undated).
Austenal; Thermoflex; Flexible Restorative for Dentistry; 1 page (undated).
MICRODENTAL; Give your Patients a Metal Free Smile with Dental D; 2 pages (undated).
LMT; Lab Management Today; Acetal Resin Injection System; 2 pages (undated).
Austenal; Thermoflex; Metal Free Esthetics; 2 pages (undated).
Austenal; Thermoflex; No Metal; 2 pages (undated).
Austenal; Thermoflex; The First Choice In Metal–Free Esthetics; 4 pages insert containing pricing—1 page (undated).
MicroSelect, Inc.; Dental D; Producing natural–looking results for more applications with Dental D; 1999; 2 pages.
Dental D—Metal–free removables, Contemporary Esthetics and Restorative Practice 1998;2(6): 52, 56–57. Tech–Specs.
Huggett et al; J. Dent. 1986; "The use of nylon as a denture–base material" pp. 18–22.
MacGregor et al; Journal of Dentistry, 12 No. 2 1984; "Recent experiences with denture polymers"; pp. 146–157.

* cited by examiner

Primary Examiner—Leo B. Tentoni
(74) Attorney, Agent, or Firm—Dale R. Lovercheck; James B. Bieber

(57) ABSTRACT

The invention provides a method of making a removable partial dental prosthesis by molding a removable partial dental prosthesis having a base, an artificial tooth and a clasp. The artificial tooth is supported by said base. The base is integrally connected to the clasp. The base includes pigment and is substantially opaque. The clasp is effectively free of pigment and is substantially transparent. The base is formed to mate with oral mucosa for support of the prosthesis thereon.

4 Claims, 3 Drawing Sheets

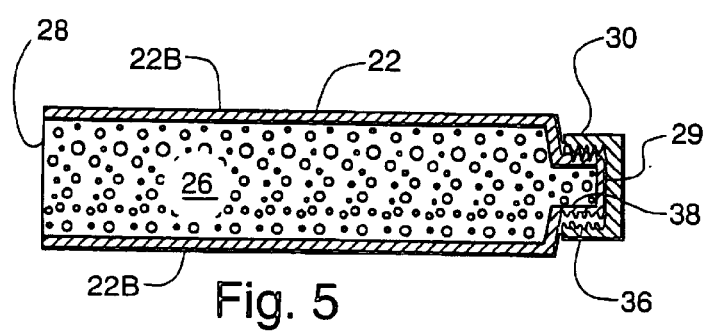
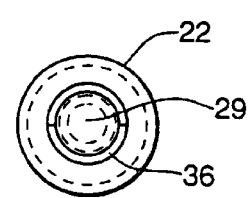
Fig. 5  Fig. 6
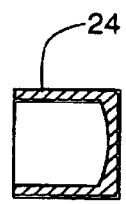
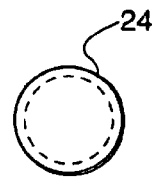
Fig. 7  Fig. 8

PROCESS OF MAKING A DENTAL PROSTHESIS

This is a continuation of U.S. patent application Ser. No. 09/362,364 filed Jul. 28, 1999 now abandoned.

The invention relates to dental devices, denture products, kits, systems and methods therefor. The invention provides a dental device such as a denture base, clasp, denture and partial denture. The invention provides kits, systems and methods for molding dentures having clasps. The invention provides a semi-crystalline transparent clasp, and partial dentures having a transparent clasp. This invention provides removable partial denture having clasps composed of a transparent semi-crystalline polyamide formed by an injection molding.

BACKGROUND OF THE INVENTION

Thermoplastic partial denture clasps have been fabricated with pigmented polyamide/copolymer, polyacetal, which have poor aesthetic properties, and transparent 'amorphous' polymer compounds, which results in poor physical properties and require laborious fabrication methods. Amorphous polyamides display a clear and colorless quality however; very high viscosities and poor physical/mechanical properties preclude their use as injection molded dental resins.

Removable partial dental prostheses are employed to restore one or more, but not all, of the natural teeth of a patient. The primary objectives of a properly designed dental prosthesis include the preservation of remaining teeth, along with hard and soft oral tissue, the restoration of oral function, and the restoration of dental and facial aesthetics.

Removable partial dental prostheses are commonly formed with a base or saddle which rests on the oral mucosa in an edentulous space and is coupled by connector means to one or more abutment teeth, that is, a tooth which abuts or is adjacent to the edentulous space.

Perhaps one of the most common forms of partial dental prosthesis is the distal extension removable partial denture which is used to replace posterior teeth with artificial teeth on one or both sides of the mouth. Distal extensions are commonly secured to an abutment tooth by clasps, which are mounted on the abutment tooth to provide for stabilization and retention of the prosthesis, and a connector, which extends between the clasp and the base of the distal extension. The base or saddle of the distal extension rests on the alveolar ridge.

Prefabricated clear and tooth colored thermoplastic clasps are described in U.S. Pat. No. 5,102,337. The prefabricated clasps are contoured by applying heat to the area which the technician wishes to shape and bend. Kulwiec et al. In U.S. Pat. No. 4,412,824 discloses removable partial dental prosthesis and method of forming and supporting the same.

Prior art dental devices have low impact strength. These problems of the prior art are overcome by the present invention. The prior art does not disclose a dental device including thermoplastic polyamide having a Charpy notched impact strength of at least 3.5, or a dental device including polyamide having at least 10 percent by weight of micro-crystals having a largest dimension less than 750 nanometers, as provided by the present invention.

OBJECTS OF THE INVENTION

It is an object of the invention to provide a dental device including thermoplastic polyamide having a Charpy notched impact strength of at least 3.5.

It is an object of the invention to provide a dental device including polyamide having at least 10 percent by weight of micro-crystals having a largest dimension less than 750 nanometers.

It is an object of the invention to provide a metal cartridge container containing particles of thermoplastic polyamide effectively free of pigment.

It is an object of the invention to provide a method of making a partial dental prosthesis having a substantially transparent clasp, by injecting substantially transparent thermoplastic into a first portion of a mold cavity of a mold containing an artificial tooth, and injecting substantially opaque thermoplastic into a second portion of the mold cavity.

It is an object of the invention to provide a removable partial dental prosthesis including an artificial tooth supported by a base integrally connected to a clasp, wherein the base includes pigment and is substantially opaque, and the clasp is substantially transparent and effectively without pigment.

It is an object of the invention to provide a kit for making a denture, including: a package supporting a first cartridge enclosing pigment and first particles of thermoplastic and a second cartridge enclosing second particles of thermoplastic effectively free of pigment.

It is an object of the present invention to provide a removable partial dental prosthesis which is capable of restoring oral function and dental and facial aesthetics without destruction of adjacent teeth and soft oral tissue.

Another object of the present invention is to provide a method of supporting a removable partial dental prosthesis in the mouth and particularly on the alveolar ridge which greatly reduces stress on the ridge and abutment teeth.

Still a further object of the present invention is to provide a method for the manufacture or formation of removable partial dentures which is adaptable to denture manufacturing techniques and yet includes structure providing enhanced performance of the prosthesis.

Another object of the present invention is to provide a method for supporting a dental prosthesis which enhances the life of the remaining teeth in the mouth and which does not afford a habitat for decay and infection causing debris.

It is also an object of the present invention to provide a dental prosthesis which is compact, relatively easy to manufacture, highly durable, and distributes and redirects localized stress forces.

The removable dental prosthesis and method of the present invention have other objects and features of advantage which will become more apparent from and are set forth in the following description of the preferred embodiment and the accompanying drawings.

Opacity as used herein refers to the percentage of impinging white light transmitted from a spectrophotometer through a 1 mm thick sample of material being tested.

Charpy notched impact strength as used herein refers to Notched impact strength in foot-pounds/inch$^2$ (ft-lb/in$^2$) measured by ISO 179:1993

SUMMARY OF THE INVENTION

The invention provides a metal cartridge container containing particles of thermoplastic polyamide effectively free of pigment. The metal cartridge is used in a method of making a partial dental prosthesis having a substantially transparent clasp. First a substantially transparent thermoplastic is injected into a first portion of a mold cavity of a mold containing an artificial tooth, and then a substantially opaque thermoplastic injecting into a second portion of the mold cavity. The removable partial dental prosthesis formed includes an artificial tooth supported by a base integrally connected to a clasp, wherein the base includes pigment and is substantially opaque, and the clasp is substantially transparent and effectively without pigment. The invention provides a dental device including thermoplastic polyamide having a Charpy notched impact strength of at least 3.5 ft-lb/in$^2$. Preferably the polyamide comprises at least 10 percent by weight of micro-crystals having a largest dimension less than 750 nanometers, and has an opacity less than 50%. More preferably the polyamide comprises at least 20 percent by weight of micro-crystals having a largest dimension less than 750 nanometers, and has a Charpy notched impact strength of at least 4.5 ft-lb/in$^2$, and an opacity less than 40%. Most preferably the polyamide comprises at least 30 percent by weight of micro-crystals having a largest dimension less than 750 nanometers, and has a Charpy notched impact strength of at least 5 and an opacity less than 30%. The polyamide beneficially may have a Charpy notched impact strength of at least 6, and more beneficially may have a Charpy notched impact strength of at least 7. Preferably the device is a denture, partial denture, clasp, splint, or night guard. Preferably the polyamide has an opacity of less than 30 percent.

DESCRIPTION OF THE DRAWING

FIG. 5 is a cross-section side view of a cartridge container tube enclosing polyamide from a kit for making a partial denture in accordance with the present invention.

FIG. 6 is an end view of the cartridge container tube shown in FIG. 5 in accordance with the present invention.

FIG. 7 is a cross-section side view of a cartridge plug from a kit for making a partial denture in accordance with the present invention.

FIG. 8 is an end view of the cartridge cap shown in FIG. 7 in accordance with the present invention.

DESCRIPTION OF THE PREFERRED EMBODIMENT

Figure 1:
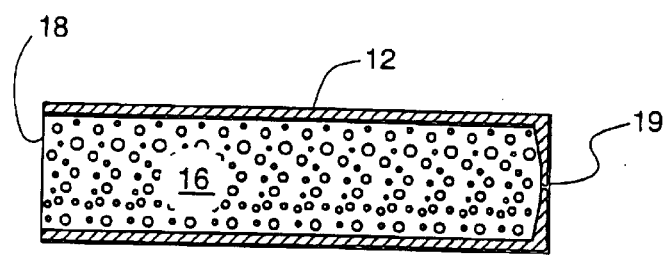
FIG. 1 is a cross-section side view of a cartridge container tube enclosing polyamide from a kit for making a partial denture in accordance with the present invention.
Figure 2:
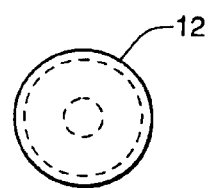
FIG. 2 is an end view of the cartridge container tube shown in FIG. 1 in accordance with the present invention.
Figure 3:
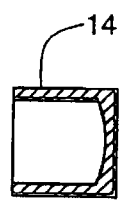
FIG. 3 is a cross-section side view of a cartridge plug which is inserted into the plug end of the cartridge container tube in accordance with the present invention.
Figure 4:
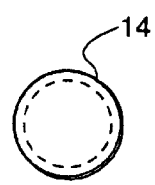
FIG. 4 is an end view of the cartridge plug shown in FIG. 3 in accordance with the present invention.

The invention is now described with more particular reference to FIGS. 1–10. With more particular reference to FIGS. 1–4 is seen cartridge container 12 and cartridge plug 14 enclosing nylon pellets 16. Plug 14 is inserted into plug end 18 of container 12. During shipping and storage cartridge container 12 with cartridge plug 14 inserted plug end 18 encloses nylon pellets 16. In use cartridge container 12, cartridge plug 14 and nylon pellets 16 are heated to melt the nylon pellets16 to form liquid nylon. The liquid nylon is pressed through burstable end 19 into a mold from cartridge container 12.

With more particular reference to FIGS. 5–8 is seen cartridge container 22 and cartridge plug 24 enclosing nylon pellets 26. Plug 24 is inserted into plug end 28 of container 22. During shipping and storage cartridge container 22 with cartridge plug 24 inserted plug end 28 encloses nylon pellets 26. Cap 30 is supported by threaded nozzle 36. Nozzle inner wall 38 encloses an output channel. In use cartridge container 22, cartridge plug 24 and nylon pellets 26 are heated to melt the nylon pellets26 to form liquid nylon. The liquid nylon is pressed through the output channel and burstable end 29 into a mold from cartridge container 22.

Figure 9:
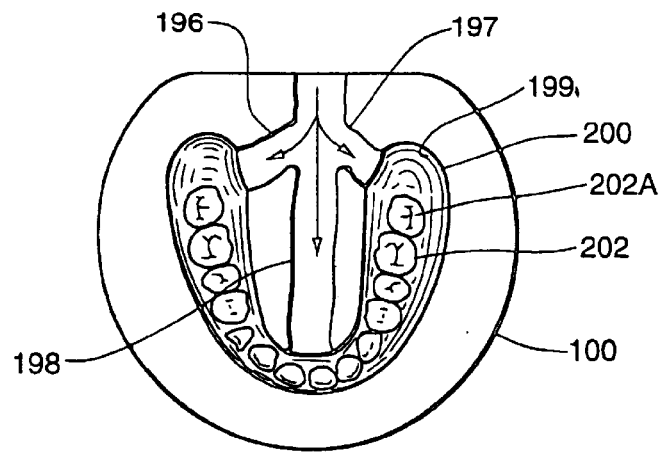
FIG. 9 is a view of an injection mold with sprues for use in accordance with the present invention.
Figure 10:
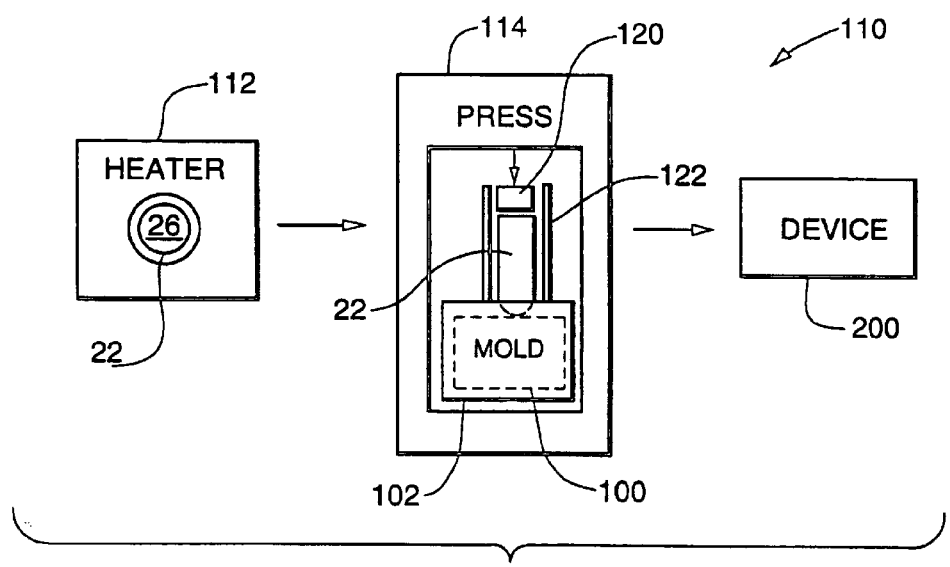
FIG. 10 is a schematic diagram of a system for making molded dental devices from polyamide enclosed in a cartridge container tube in accordance with the present invention.

With more particular reference to FIGS. 9–10 is seen a mold 100 and a system 110 for making molded dental devices 200 from polyamide 26 enclosed in a cartridge container tube 22. Polyamide 26 enclosed in a cartridge container tube 22 is heated in heater 112. Cap 30 is removed from threaded nozzle 36. Threaded nozzle 36 is positioned under ram 120 in guide 122 of press 114 to force burstable end 29 to open the output channel of nozzle inner wall 38 into mold 100 when pressure is applied to polyamide 26 enclosed in a cartridge container tube 22. Mold 100 is supported by metal flask 102. Mold 100 has molded artificial teeth 202A and 202 supported therein and made of an acrylic interpenetrating polymer network (IPN). Ram 120 is moved down pressing cartridge plug 24 down. As Ram 120 moves down pressing cartridge plug 24 down cartridge container tube 22 is crushed and pressure is applied to heated polyamide 26 pushing polyamide 26 through passage 196, 197 and 198 into a mold cavity wall 199 enclosing a mold cavity within mold 100 to form dental device 200 having molded polyamide 26 and artificial teeth 202. The mold cavity within mold 100 has the shape of dental device 200. Mold 100 is removed from press 114 and metal flask 102. From mold 100 is removed dental device 200 having molded polyamide 26.

The transparent polymer used in clasps made in accordance with the invention preferably consists of a permanently transparent, chemical and stress crack resistant, high impact strength, UV and visible light stable, low water sorption, dimensionally stable, highly water resistant, steam sterilizable, semi-crystalline polyamide resin. This resin is beneficially maintains excellent physical properties while remaining permanently clear and colorless. The transparent semi-crystalline polyamide is preferably injection molded using dental flask/stone investment, a compact heating oven together with a low pressure injection molding machine (less than 90 psi) to sequentially fabricate a partial denture containing a "clear" aesthetic clasp attached to a tissue shaded base resin. The base material consists of a pigmented version of the transparent semi-crystalline polyamide resulting in a monolithic prosthetic device. Sequential injection molding of 'clear' aesthetic clasps allows for precise replication of waxed clasp design with high-strength, durable thermoplastic resin. Preferably acetal resins are used in sequential injection molding to fabricate clasps. Preferably bases are made of an opaque/pigmented semi-crystalline acetal resin.

EXAMPLE 1

23 grams of pellets of transparent crystalline nylon, Lucitone FRS crystalline nylon without pigment are poured into an aluminum container having a threaded end and then a cap is pressed onto the threaded end and supported by the threads on the threaded end of the container. The cylindrical container body is 1 inch in diameter and 3.5 inches in length. The cylindrical container body is 0.005 inch thick. The conical container end extends from the cylindrical container body and is 0.4 inch in length and has a cylindrical nozzle which is 0.375 inch in diameter. The burstable end of the nozzle is 0.4 inch thick. Transparent crystalline nylon Lucitone® FRS™ in the container is useful for injection molding to form temporary, flexible, and monomer free denture base. It is useful for the fabrication of complete or partial removable dentures as well as occlusal splints and night guards.

EXAMPLE 2

23 grams of pellets of transparent crystalline nylon, Lucitone® FRS™ crystalline nylon are coated with red pigment. The nylon pellets are poured into an aluminum container having a threaded end and then a cap is pressed onto the threaded end and supported by the threads on the threaded end of the container. The cylindrical container body is 1 inch in diameter and 3.5 inches in length. The cylindrical container body is 0.005 inch thick. The conical container end extends from the cylindrical container body and is 0.4 inch in length and has a cylindrical nozzle which is 0.375 inch in diameter. The burstable end of the nozzle is 0.4 inch thick.

Table 1 describes typical properties, of transparent crystalline nylon, Lucitone FRS used in EXAMPLES 1 and 2, and molding temperatures, and injection, heating and cooling times used in EXAMPLE 3.

TABLE 1

| | |
|---|---|
| Type and Class (according to ADA Spec. 12) | Type III, Class 1 |
| Storage temperature for powder and liquid | 60° F.–90° F. (16° C.–32° C.) |
| Dosage: | 1 cartridge (23 g) |
| Processing Time /Temp. (To reach injectable stage) | 18 minutes @ 575 F. |
| Injection Time | <1 minute |
| Material used to invest wax-up | Dental Stone |
| Cool time (prior to deflask) | 5 minutes |

EXAMPLE 3

A partial denture with a transparent clasp is prepared by:

Investment and Spruing

Soak a cast and wax up of a patients mount in water for 25 minutes prior to investing. Mix investment and embed the cast and wax-up in the lower half of a flask. Using wax sticks, D-shaped Success™ Sprue Wax Sticks (7 mm×180 mm, Item # 904584) injection sprues are built. On upper dentures, attach the sprue to the posterior border of the denture and make sure the sprue is sufficiently wide. For lower full dentures, attach the sprue to both lingual extensions as well as in the mid-line. Then embed the upper half of the flask.

Wax Elimination and Separator Application

The flask is placed in boiling water for a 4 to 6 minutes to soften the wax. The bolts on the flask are loosened and the Metal Flask Brackets are removed. The flask is opened and the Space Maintainer is removed. Then a boil out procedure is completed to form a clasp mold and the wax is discarded.

The flask is placed in boiling water for a 4 to 6 minutes to soften the wax. The bolts on the flask are loosened and the Metal Flask Brackets are removed. The flask is opened and the Space Maintainer is removed. Then a boil out procedure is completed to form a partial denture mold and the wax is discarded.

The molds are flushed with clean boiling water. Bevel the stone with a lab knife around the mouth of the sprue. The flask margin and cavities are checked to ensure that both flask halves fit together with intimate metal contact. A thin coat of Al-Cote® Separating Agent is applied to the model and the model is allowed to dry completely. Mechanical retention is added by grinding diatorics into the teeth. Thermoplastic Injection Insert is positioned on one side of the flask and the flask halves are placed under an infrared heat source.

Clear Clasp Fabrication

The clasp is waxed to full contour, slightly over building the body of the clasp. All excess model is trimmed away, leaving a small core with the clasp attached. Two clasps are fabricated. Investment and spruing are completed. Wax is eliminated. Clear transparent Lucitone® FRS™ crystalline nylon is Injected into the mold to form the clasps while heating.

Heating and Injection

After removing the cap from a cartridge, formed by following the procedure of EXAMPLE 1, the container of transparent Lucitone FRS crystalline nylon is placed in an injection sleeve to form an assembly. When the container of transparent Lucitone FRS crystalline nylon is placed in an injection sleeve the threaded end of the container is positioned in the injection sleeve to face away from the injection sleeve handle. A sleeve plug is placed into the remaining space in the heating sleeve. The assembly is inserted into a cartridge furnace (preheated to 575° F.) and a timer is set for 18 minutes. While heating the assembly in the furnace for 18 minutes, the flask halves are assembled and placed in front of the Success Injection System manufactured and sold by Dentsply. The sleeve assembly is removed from the furnace and positioned on top of the flask such that the threaded end of the container fits into the opening of a thermoplastic injection insert to form a combination. The combination is then slid into the Success Injection System and the piston is engaged to press the transparent Lucitone FRS crystalline nylon from the container into the clasp mold enclosed by the flask. Injection into the mold is complete within one (1) minute. Then the flask and sleeve assembly combination is removed from the Injection system. The heating sleeve is then twisted off of the flask and the used container is expelled from the heating sleeve using a knock out base and knock out rod. The injected flask is deflasked five minutes after injection. The clear clasps are finished to final contour with carbide burrs and the clasps are fitted to denture mold. After removing the cap from a cartridge, formed by following the procedure of EXAMPLE 2, the container of pigmented Lucitone FRS crystalline nylon is placed in an injection sleeve to form an assembly. When the container of pigmented Lucitone FRS crystalline nylon is placed in an injection sleeve the threaded end of the container is positioned in the injection sleeve to face away from the injection sleeve handle. A sleeve plug is placed into the remaining space in the heating sleeve. The assembly is inserted into a cartridge furnace (preheated to 575° F.) and a timer is set for 18 minutes. While heating the assembly in the furnace for 18 minutes, the flask halves are assembled and placed in front of the Success Injection System manufactured and sold by Dentsply. The sleeve assembly is removed from the furnace and positioned on top of the flask such that the threaded end of the container fits into the opening of a thermoplastic injection insert to form a combination. The combination is then slid into the Success Injection System and the piston is engaged to press the pigmented Lucitone FRS crystalline nylon from the container into a partial denture mold enclosed by the flask. Injection into the partial denture mold is complete within one (1) minute. Then the flask and sleeve assembly combination is removed from the Injection system. The heating sleeve is then twisted off of the flask and the used container is expelled from the heating sleeve using a knock out base and knock out rod. The injected flask is deflasked five minutes after injection.

Finishing and Polishing

The flexible partial denture with a transparent clasp is finished using coarse pumice and polished using Tripoli TM polishing compound and High Shine TM polishing compound.

EXAMPLE 4

A full denture is prepared by:

Investment and Spruing

Soak a cast and wax up of a patients mount in water for 25 minutes prior to investing. Mix investment and embed the cast and wax-up in the lower half of a flask. Using wax sticks, D-shaped Success™ Sprue Wax Sticks (7 mm×180 mm, Item # 904584) injection sprues are built. On upper dentures, attach the sprue to the posterior border of the denture and make sure the sprue is sufficiently wide. For lower full dentures, attach the sprue to both lingual extensions as well as in the mid-line. Then embed the upper half of the flask.

Wax Elimination and Separator Application

The flask is placed in boiling water for a 4 to 6 minutes to soften the wax. The bolts on the flask are loosened and the Metal Flask Brackets are removed. The flask is opened and the Space Maintainer is removed. Then a boil out procedure is completed to form a clasp mold and the wax is discarded.

The flask is placed in boiling water for a 4 to 6 minutes to soften the wax. The bolts on the flask are loosened and the Metal Flask Brackets are removed. The flask is opened and the Space Maintainer is removed. Then a boil out procedure is completed to form a full denture mold and the wax is discarded.

The molds are flushed with clean boiling water. Bevel the stone with a lab knife around the mouth of the sprue. The flask margin and cavities are checked to ensure that both flask halves fit together with intimate metal contact. A thin coat of Al-Cote® Separating Agent is applied to the model and the model is allowed to dry completely. Mechanical retention is added by grinding diatorics into the teeth. Thermoplastic Injection Insert is positioned on one side of the flask and the flask halves are placed under an infrared heat source.

After removing the cap from a cartridge, formed by following the procedure of EXAMPLE 2, the container of pigmented Lucitone FRS crystalline nylon is placed in an injection sleeve to form an assembly. When the container of pigmented Lucitone FRS crystalline nylon is placed in an injection sleeve the threaded end of the container is positioned in the injection sleeve to face away from the injection sleeve handle. A sleeve plug is placed into the remaining space in the heating sleeve. The assembly is inserted into a cartridge furnace (preheated to 575° F.) and a timer is set for 18 minutes. While heating the assembly in the furnace for 18 minutes, the flask halves are assembled and placed in front of the Success Injection System manufactured and sold by Dentsply. The sleeve assembly is removed from the furnace and positioned on top of the flask such that the threaded end of the container fits into the opening of a thermoplastic injection insert to form a combination. The combination is then slid into the Success Injection System and the piston is engaged to press the pigmented Lucitone FRS crystalline nylon from the container into adenture mold enclosed by the flask. Injection into the denture mold is complete within one (1) minute. Then the flask and sleeve assembly combination is removed from the Injection system. The heating sleeve is then twisted off of the flask and the used container is expelled from the heating sleeve using a knock out base and knock out rod. The injected flask is deflasked five minutes after injection.

Finishing and Polishing

The flexible denture is finished using coarse pumice and polished using Tripoli TM polishing compound and High Shine TM polishing compound.

TABLE 2 shows physical properties of the products of Examples 3 and 4 and. The products of Examples 3 and 4 have more than 50 percent greater Charpy notched impact strength than commercially marketed dental products.

TABLE 2

| Property | Examples 3 and 4 |
|---|---|
| Formulation | Microcrytalline polyamide |
| Tensile strength (psi) | 9000 |
| Tensile Modulus (psi) | 232000 |
| Flexural Strength (psi) | 9300 |
| Flexural Modulus (psi) | 200000 |
| Charpy notched ft-lb/in$^2$ | 7.6 |
| Charpy unnotched | No break |
| Specific Gravity | 1.06 |
| Melt point C. | 248 |
| Glass transition $T_g$ C | 155 |
| Melt flow (g/10 min) | N/A |
| Water Absorption % 24 hrs | .45 |

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method for making a removable partial dental prosthesis comprising:

molding a removable partial dental prosthesis having a base, an artificial tooth and a clasp, said artificial tooth being supported by said base, said base being integrally connected to said clasp, said base comprising pigment and being substantially opaque, said clasp being effectively free of pigment and being substantially transparent, said base being formed to mate with oral mucosa for support of said prosthesis thereon.

2. The method of claim 1 further comprising providing a first enclosure enclosing first particles of thermoplastic in a first cartridge said first cartridge enclosing pigment, providing a second enclosure enclosing second particles of thermoplastic in the second cartridge, said second cartridge being effectively free of pigment, and wherein said base is formed by injection molding first particles of thermoplastic and said clasp is formed by injection molding second particles of thermoplastic.

3. A method for making a removable partial dental prosthesis, comprising:

providing a mold having a mold cavity and containing said artificial tooth, injecting substantially transparent thermoplastic into a first portion of said mold cavity, and injecting substantially opaque thermoplastic into a second portion of said mold cavity, removing said removable partial dental prosthesis from said mold, removable partial dental prosthesis having an artificial tooth and an opaque base comprising pigment integrally connected to a substantially transparent clasp.

4. A method for making a dental prosthesis comprising:

injection molding a dental prosthesis having a base, an artificial tooth and a clasp, said base being integrally connected to said clasp, said artificial tooth being supported by said base, said base comprising pigment and being substantially opaque, said clasp being effectively free of pigment and being substantially transparent, said base being formed to mate with oral mucosa for support of said prosthesis thereon.

* * * * *